United States Patent [19]

Lutsey et al.

[11] Patent Number: 4,534,722
[45] Date of Patent: Aug. 13, 1985

[54] FORMING AND CONVEYING OF BAKED CONFECTION SHELLS

[75] Inventors: Thomas H. Lutsey; Vernon L. Bero, both of Green Bay, Wis.

[73] Assignee: Gold Bond Ice Cream, Inc., Green Bay, Wis.

[21] Appl. No.: 600,764

[22] Filed: Apr. 16, 1984

[51] Int. Cl.³ .............................. A21C 9/00; A21C 15/02
[52] U.S. Cl. ............................... 425/104; 99/353; 99/426; 425/92; 425/383; 425/403.1; 425/404; 425/438
[58] Field of Search ............... 425/90, 94, 99, 100, 425/103, 104, 319, 383, 391, 402, 92, 403.1, 404, 438; 99/353, 426

[56] References Cited

U.S. PATENT DOCUMENTS

| | | | |
|---|---|---|---|
| 2,603,143 | 7/1952 | Saenz | 99/353 |
| 3,680,474 | 8/1972 | Brown | 99/353 |
| 3,690,895 | 9/1972 | Amadon et al. | 99/353 |
| 3,763,764 | 10/1973 | Schy | 99/353 |
| 3,766,846 | 10/1973 | Jimenez | 99/353 |
| 3,861,289 | 1/1975 | Baker et al. | 99/353 |
| 3,869,971 | 3/1975 | Driscoll | 99/353 |
| 3,993,788 | 11/1976 | Longenecker | 426/502 |
| 4,197,793 | 4/1980 | Hanson et al. | 99/352 |

*Primary Examiner*—Willard E. Hoag
*Attorney, Agent, or Firm*—Andrus, Sceales, Starke & Sawall

[57] ABSTRACT

A machine is provided which includes a pick-up station adapted to receive flat confection discs from a baking machine, and feed them in succession to a rotary wheel at a forming station to lap fold the discs into taco shape. A fixed elongated support rail having a curved upper surface extends generally the length of the conveyor and receives the folded shells thereover so that the shells hang therefrom. An endless belt is coextensive with the support rail and biasingly holds the formed shells to the rail and frictionally drives the shell freely slidingly therealong. A pair of shell leg receiving channels are disposed beneath the support rail, with the channels formed by inner and outer generally parallel walls coextensive with the rail. The inner walls are defined by a support device beneath the rail while the outer walls are formed by plates which are transversely adjustable to thereby control the channel width and shell leg angle. In the embodiment disclosed, the support rail and support device are tubular and fluid flows therethrough to cool and harden the formed shells. The traveling folded shells are subjected to an oil spray which tends to make the shells remain crisp and generally impervious to moisture from a subsequently applied filling. Furthermore, the drive belt is cooled adjacent the shell discharge to counteract belt expansion covered by engagement with the hot baked shells.

19 Claims, 8 Drawing Figures

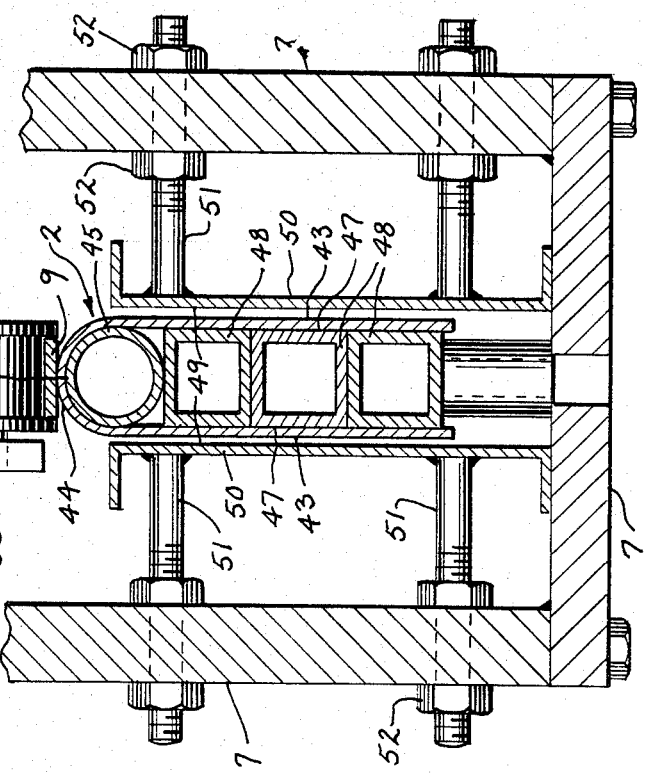
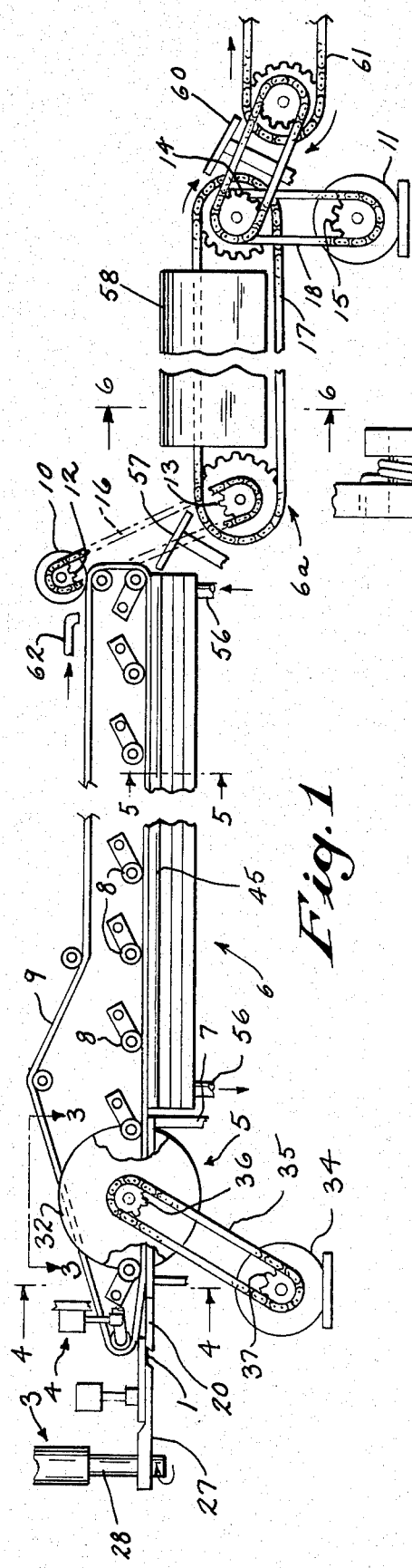
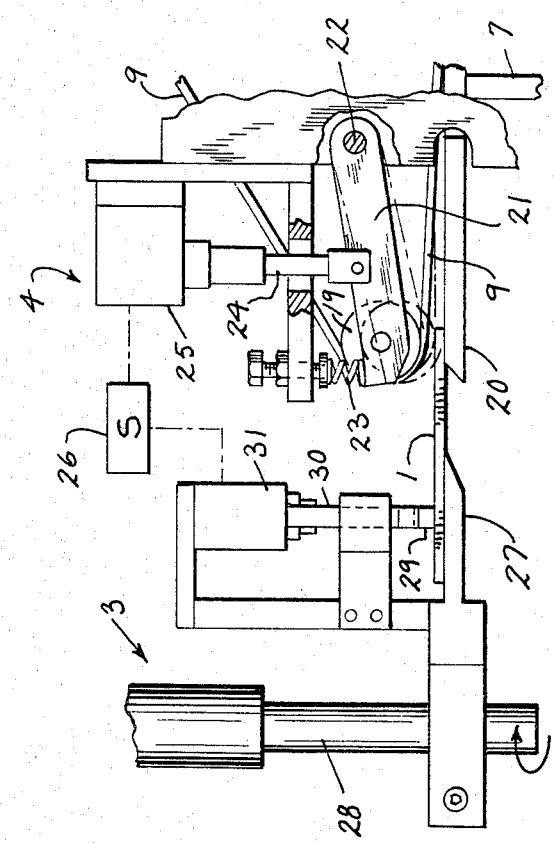

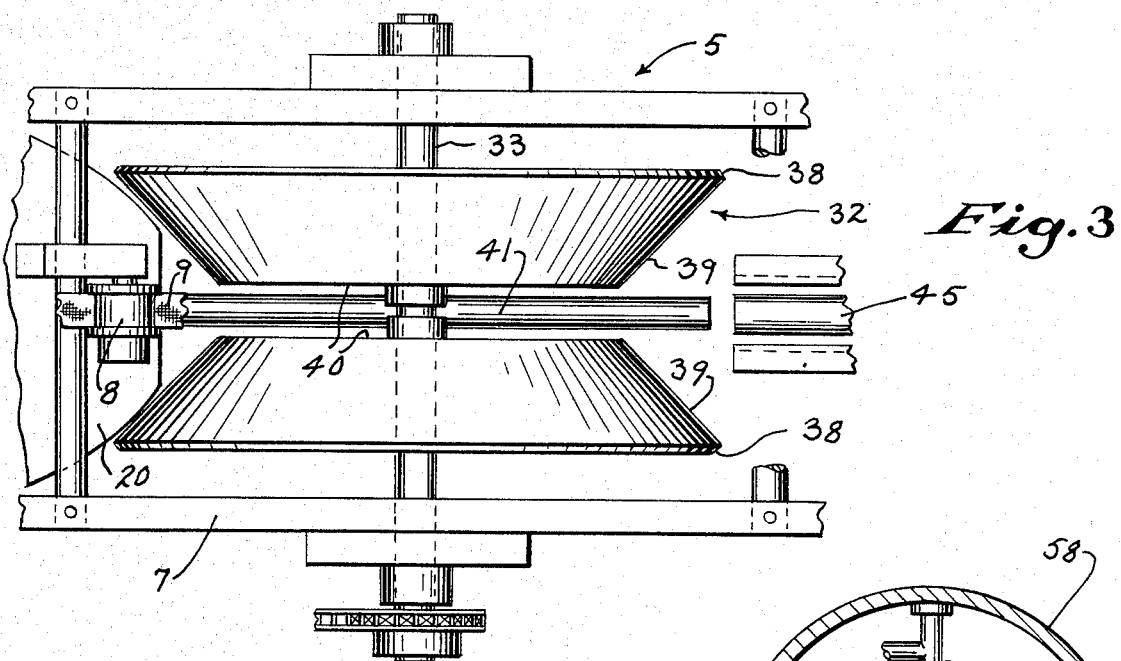
Fig. 3
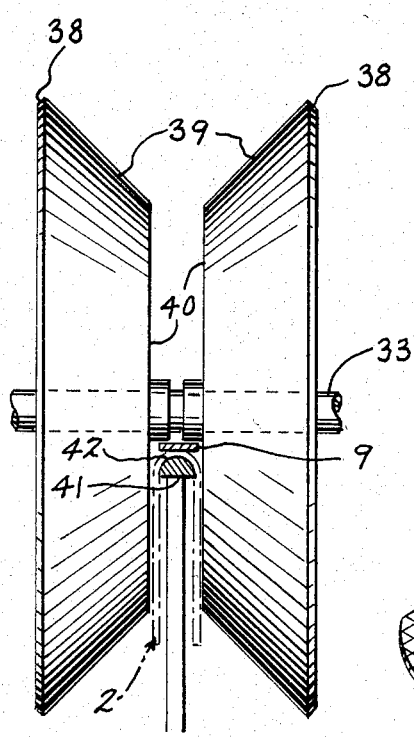
Fig. 4
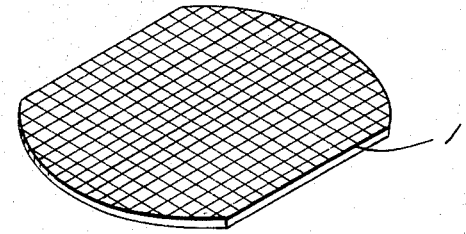
Fig. 6
Fig. 7
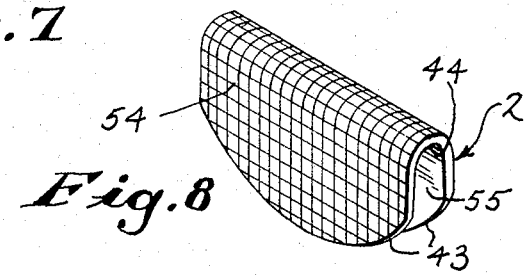
Fig. 8

4,534,722

FORMING AND CONVEYING OF BAKED CONFECTION SHELLS

BACKGROUND AND SUMMARY OF THE INVENTION

This invention relates to forming and conveying of baked confection shells.

A recent development in frozen confections is the provision of a sandwich-like item which comprises a sugar shell shaped like a taco shell and which is filled with ice cream or the like and suitably coated with topping, chips etc. if desired. While the shell resembles a taco shell made from a lap folded tortilla, it actually is constituted of different ingredients such as those used in a sugar based cookie cone. Such cones are often made by baking a plurality of flat discs in succession in a suitable baking machine and then forming each baked disc, while in relatively soft condition, on rotating ice cream cone shaped dies.

It is an object of the present invention to provide a shell forming and conveying machine for use at the discharge of a baking machine to create taco-like confection shells from baked discs.

It is a further object of the invention to form the discs into taco-like shape and then convey them downstream in a simple manner for further processing.

It is yet another object of the invention to control and fix the shape of the formed shells during conveying, and to treat the shells so that they remain crisp when subsequently filled with ice cream or the like.

It is an additional object to at least partially prevent the conveying mechanism from being adversely affected by the high temperature of the baked shells.

In accordance with the various aspects of the invention, a machine is provided which includes a pick-up station adapted to receive flat confection discs from a baking machine, and feed them in succession to a rotary wheel at a forming station to lap fold the discs into taco shape. A fixed elongated support rail having a curved upper surface extends generally the length of the conveyor and receives the folded shells thereover so that the shells hang therefrom. An endless belt is coextensive with the support rail and biasingly holds the formed shells to the rail and frictionally drives the shell freely slidingly therealong.

A pair of shell leg receiving channels are disposed beneath the support rail, with the channels formed by inner and outer generally parallel walls coextensive with the rail. The inner walls are defined by a support device beneath the rail while the outer walls are formed by plates which are transversely adjustable to thereby control the channel width and shell leg angle. In the embodiment disclosed, the support rail and support device are tubular and fluid flows therethrough to cool and harden the formed shells.

The traveling folded shells are subjected to an oil spray which tends to make the shells remain crisp and generally impervious to moisture from a subsequently applied filling.

Furthermore, the drive belt is cooled adjacent the shell discharge to counteract belt expansion caused by engagement with the hot baked shells.

BRIEF DESCRIPTION OF THE DRAWINGS

The accompanying drawings illustrate the best mode presently contemplated by the inventors for carrying out the invention.

In the drawings:

FIG. 1 is a schematic side elevation of a forming and conveying machine adapted to incorporate the various aspects of the invention;

FIG. 2 is an enlarged fragmentary showing of the shell pick-up station adjacent the discharge end of the baking machine;

FIG. 3 is a plan view of the shell forming wheel, taken on line 3—3 of FIG. 1;

FIG. 4 is a front end view of the wheel taken on line 4-4 of FIG. 1;

FIG. 5 is a transverse section through the conveyor taken on line 5—5 of FIG. 1;

FIG. 6 is a transverse section taken on line 6—6 of FIG. 1 and showing the oil spray;

FIG. 7 is a perspective view of a baked confection disc; and

FIG. 8 is a perspective view of the formed taco-like shell.

DESCRIPTION OF THE PREFERRED EMBODIMENT

The concepts of the invention are directed to processing a baked disc of sugar-based confection material, shown at 1 in FIG. 7, into a taco-shaped shell shown at 2 in FIG. 8 and which is suitable for filling with ice cream or the like.

FIG. 1 shows a discharge station 3 for a disc baking machine of any suitable type, not shown, and which feeds into a disc pick-up station 4. The disc is then passed to a forming station 5 wherein it is formed into a shell, and then moved along conveyors 6, 6a for further processing before discharge.

The device includes a frame 7 on which is mounted a plurality of rollers 8 over which are trained a narrow flat endless belt 9 which extends along conveyor 6. Belt 9 has a friction surface thereon and is driven by a drive roller 10 which is connected to a motor 11 through a series of sprockets 12–15 and chains 16–18. Belt 9 extends from pick-up station 4 to the discharge end of conveyor 6, with its lower flight adapted to engage the baked confection.

Referring to FIG. 2, the upstream end portion of belt 9 is trained over a clamping roller 19 which is adapted to clamp the belt successively against baked confection discs 1 placed on a table 20 forming part of pick-up station 4. For this purpose, roller 19 is mounted to one end of a lever arm 21, with the other arm end being pivotally mounted to frame 7, as at 22. Lever arm 21 is biased downwardly by a spring 23 and is connected to a centrally mounted plunger 24 which in turn is vertically actuated by a solenoid 25 of any well-known type. Solenoid 25 is controlled by an automatic sequencing switch 26 to raise and lower arm 21.

The baking machine discharge station 3 includes a table 27 swingable about a vertical shaft 28 by any suitable camming mechanism. A disc clamping means is disposed above table 27 and comprises a clamp 29 disposed on the end of a plunger 30 which is actuated by a solenoid 31 which is also controlled by sequencing switch 26.

The arrangement is such that clamp 29 grabs a disc 1 from the baking machine and table 20 is then swung around to the position shown to position disc 1 at least partially over pick-up table 20. At the same time, plunger 24 is in retracted position with the upstream end of belt 9 spaced from table 20. Once a disc 1 is over table 20, plunger 30 snappingly retracts to release clamp 29 from the disc and plunger 24 simultaneously snappingly extends to cause belt 9 to grab the disc and drivingly feed it to forming station 5. The position of plungers 24 and 30 is then reversed so that the next disc 1 may be positioned and fed forwardly.

Referring to FIGS. 1, 3 and 4, forming station 5 comprises a forming wheel 32 which is mounted on a transverse shaft 33 and rotatably driven from a motor 34 via a chain 35 and sprockets 36, 37. Forming wheel 32 comprises a pair of axially spaced facing annular dish-shaped roller elements 38 having inwardly inclined side walls 39 and facing parallel bottom walls 40. A longitudinally extending rod 41 is disposed between elements 38 closely beneath shaft 33 and extends from table 20 to adjacent conveyor 6. The upper surface 42 of rod 41 is curved. Belt 9 is positioned between shaft 33 and rod 41 and is coextensive with the latter.

As belt 9 drives confection disc 1 into station 5 from station 4, the hot baked, relatively soft disc engages rotating walls 39 and 40 and is lap folded so that it drops in hanging relationship onto rod 41, as shown in FIG. 4, now assuming the taco shell shape of FIG. 8 having two downwardly hanging legs 43 joined by a folded portion 44.

Shell 2 is now driven by belt 9 into conveyor 6. Referring to FIGS. 1 and 5, conveyor 6 includes a smooth elongated longitudinally extending hollow shell support rail 45 which is fixedly mounted to frame 7 and is coextensive with and disposed closely beneath belt 9. Rail 45 commences adjacent the downstream end of rod 41 and is provided with a curved upper surface 46 which approximates the inner curvature of folded portion 44 of shell 2.

Channel means are provided to receive the downwardly hanging legs 43 of shell 2. The inner channel walls are defined by the outer faces 47 of a support device comprising a plurality of stacked tubes 48 fixedly mounted to frame 7 beneath rail 45. The outer channels walls are defined by the inner faces 49 of a pair of spaced parallel plates 50. Plates 50 are generally parallel to faces 47 and are mounted for adjustment transversely of the conveyor, as by bolts 51 welded to the plates and mounted to upstanding walls of frame 7 by nuts 52 threaded thereon. The adjustment provides a means to limit spreading of shell legs 43 to a desired spacing during conveying so that the width of shell 2 is precisely controlled. This is important to enable the shells to subsequently be properly fit into forms at the time of later filling.

When shells 2 enter conveyor 6, they are frictionally slid down rail 45 by the lower flight of belt 9, which is biased toward the rail by spring loading of rollers 8, as at 53. Shells 2 themselves are formed to assist in the friction driving of belt 9 and in the free sliding along rail 45. For this purpose, and as best shown in FIG. 8, the outer faces 54 of shell 2 is provided with an uneven friction surface such as by waffling, for engagement by belt 9, while the inner face 55 which engages rail 45 is smooth.

Depending upon the length of the conveyor, it may be desirable to provide an assist to the cooling of the hot baked shells as they travel therealong, and not rely solely on the ambient air. Therefore, and in the present embodiment, rail 45 and tubes 48 are connected through pipes 56 to a suitable pressurized source of cooling fluid such as water which flows through the rail and tubes and serves to cool the shells.

Furthermore, when shells 2 are to be filled with ice cream or other material having a high moisture content, it is desirable to treat the shells so that they will stay crisp and not permit moisture to significantly penetrate into their interiors. For this purpose, the shells are treated with an oil spray. In the present embodiment, and referring to FIGS. 1 and 6, the spray is provided at a second conveyor section 6a which is downstream of and forms an extension to conveyor section 6. At the discharge of conveyor 6, shells 2 slide off rail 45 and down a ramp or slide 57 and will hangingly fall onto traveling chain 17 which then carries them through a hood 58. A plurality of spray nozzles 59 are disposed within hood 58 and positioned to spray oil onto both the exterior and the interior of shells 2 to saturate them and make them generally impervious to moisture. Nozzles 59 are supplied with pressurized oil from any suitable well-known source.

Shells 2 may then be discharged from conveyor section 6a, such as onto a further slide 60 and hence to a discharge conveyor 61.

It has been found that the lower flight of belt 9 of conveyor 6 tends to undesirably stretch due to its being subjected to direct contact with the hot baked shells 2. Such stretching may cause belt 9 to come loose from its guide rollers 8, especially on the return flight. Means are therefore provided to cool the upper or return flight of belt 9 so that it shrinks back to its normal shape. In the present embodiment, and as shown in FIG. 1, a nozzle 62 is mounted adjacent drive rollers 10 and is adapted to discharge cold air onto belt 9. Nozzle 62 may be supplied with said air from any suitable well-known source.

Various modes of carrying out the invention are contemplated as being within the scope of the following claims particularly pointing out and distinctly claiming the subject matter which is regarded as the invention.

We claim:

1. An apparatus for forming and conveying hot baked shells for use in confections, comprising, in combination:
  (a) pick-up means for receiving a plurality of hot baked relatively soft confection discs in successions and for feeding said discs in a longitudinal direction,
  (b) rotary forming means disposed downstream of said pick-up means for receiving said discs therefrom and for forming said hot baked discs into lap folded taco-shaped shells having generally parallel spaced legs joined by a folded portion,
  (c) an elongated fixed conveyor rail extending downstream from said forming means for receiving said shells therefrom so that said shells hang from said rail,
  (d) and driven belt means disposed above and generally coextensive with said conveyor rail for frictionally engaging and slidingly driving said hanging shells progressively along said rail toward a discharge point.

2. The apparatus of claim 1 which includes:
  (a) spaced channel means disposed below said rail for passage of said shell legs therethrough, (b) and means associated with said channel means for adjustably limiting the space between said shell legs during shell travel along said conveyor rail.

3. The apparatus of claim 2 in which each of said spaced channel means is defined by:
 (a) a support device disposed beneath said conveyor rail and forming an inner channel wall,
 (b) and a plate spaced transversely outwardly of said support device and forming an outer channel wall generally parallel to said inner channel wall.

4. The apparatus of claim 3 in which said means for adjustably limiting the space between said shell legs comprises means mounting said plate for selective adjustment relative to said support device.

5. The apparatus of claim 1 which includes shell cooling means coextensive with said conveyor rail.

6. The apparatus of claim 5 in which said shell cooling means comprises:
 (a) a passage extending through said conveyor rail,
 (b) and means for supplying cooling fluid through said passage.

7. The apparatus of claim 6:
 (a) which includes a support device disposed beneath said conveyor rail and forming the inner walls of a pair of spaced channels for passage of said shell legs therethrough,
 (b) and wherein said shell cooling means additionally comprises passage means extending through said support device and connected to said cooling fluid supplying means for cooling said inner channels walls.

8. The apparatus of claim 1 which includes shell treating means disposed downstream of said forming means to make said shells essentially impervious to moisture.

9. The apparatus of claim 8 wherein said shell treating means comprises spray means for directing saturating oil onto baked and formed shells.

10. The apparatus of claim 9 in which said spray nozzle means is disposed to direct oil onto the exterior and interior of said shells.

11. The apparatus of claim 1:
 (a) in which said belt means is endless and has a lower flight which engages the hot shells and becomes heated, and an upper return flight,
 (b) and means disposed adjacent said return flight for cooling said heated belt means.

12. The apparatus of claim 11 in which said cooling means for said belt means comprises means for directing cooling air onto said belt means.

13. The apparatus of claim 1 in which:
 (a) said belt has a friction surface for engaging said shells and said conveyor rail is smooth,
 (b) and said shells are formed to enhance their friction contact with said belt and to enhance sliding of said shells on said rail.

14. The apparatus of claim 13 in which said shells are formed with waffled outer faces and smooth inner faces.

15. The apparatus of claim 1 in which said driven belt means extends upstream of said conveyor rail and through said forming means to the entrance to said pick-up means.

16. The apparatus of claim 15 in which said pick-up means comprises:
 (a) a table for receipt of said confection discs from a baking device,
 (b) a roller disposed above said table and over which said belt means is trained,
 (c) and means to alternately raise and lower said roller so that said belt means and said table first receive a said disc freely therebetween and then said belt means clamps said disc onto said table and drives it to said forming means.

17. The apparatus of claim 15 in which said rotary forming means comprises:
 (a) a pair of spaced forming rollers disposed on either side of said belt means,
 (b) an elongated rod disposed beneath said belt means,
 (c) and means to rotatably drive said forming rollers so that said discs driven between said rollers by said belt means are formed by said rollers into said taco-shaped shells and drop onto said rod for further transport downstream.

18. The apparatus of claim 17 in which said rollers are dish-shaped with inwardly inclined side walls and facing parallel bottom walls between which said belt means extends.

19. An apparatus for forming and conveying hot baked shells for use in confections, comprising, in combination:
 (a) pick-up means for receiving a plurality of hot baked relatively soft confection discs in succession and for feeding said discs in a longitudinal direction,
 (b) rotary forming means disposed downstream of said pick-up means for receiving said discs therefrom and for forming said hot baked discs into lap folded taco-shaped shells having generally parallel spaced legs joined by a folded portion,
 (c) an elongated fixed conveyor rail extending downstream from said forming means for receiving said shells therefrom so that said shells hang from said rail,
 (d) driven belt means disposed above and generally coextensive with said conveyor rail for frictionally engaging and slidingly driving said hanging shells progressively along said rails toward a discharge point,
 (e) spaced channel means disposed below said rail for passage of said shell legs therethrough,
 (f) means associated with said channel means for adjustably limiting the space between said shell legs during shell travel along said conveyor rail,
 (g) shell cooling means coextensive with said conveyor rail,
 (h) shell treating means disposed downstream of said forming means to make said shells essentially impervious to moisture,
 (i) said belt means being endless and having a lower flight which engages the hot shells and becomes heated, and an upper return flight,
 (j) and means disposed adjacent said return flight for cooling said heated belt means,
 (k) said belt having a friction surface for engaging said shells and said conveyor rail being smooth,
 (l) and said shells being formed to enhance their friction contact with said belt and to enhance sliding of said shells on said rail.

* * * * *